United States Patent [19]

Sarui

[11] 4,340,053

[45] Jul. 20, 1982

[54] MOLDED BODY COMPRISING VEGETABLE OIL FOR GENERATING AEROSOL FOR TREATING ATHLETE'S FOOT

[76] Inventor: Kiichiro Sarui, 26-15 Takadanobaba 4-chome, Shinjuku-ku, Tokyo, Japan

[21] Appl. No.: 199,544

[22] Filed: Oct. 22, 1980

[30] Foreign Application Priority Data

Jun. 20, 1980 [JP] Japan .................................. 55-82848

[51] Int. Cl.[3] .......................... A61F 7/00; A61K 9/70; A61K 47/00; A61M 11/00

[52] U.S. Cl. ........................................ 128/260; 36/43; 128/256; 128/268; 128/383; 219/271; 219/274; 422/305; 424/27; 424/28; 424/38; 424/40; 424/358; 428/256

[58] Field of Search ..................... 424/27, 28, 38, 358, 424/40; 36/43; 428/256; 422/305; 219/271, 274; 128/256, 260, 368, 383

[56] References Cited

U.S. PATENT DOCUMENTS

| | | | |
|---|---|---|---|
| 2,061,911 | 11/1936 | Leindorf | 424/28 |
| 2,121,604 | 6/1938 | Lynch et al. | 424/28 |
| 2,406,990 | 9/1940 | Borden | 424/27 |
| 2,602,449 | 7/1952 | Ruzsits | 128/256 |
| 2,633,846 | 4/1953 | Wray | 128/256 |
| 3,567,119 | 3/1971 | Wilbert | 424/28 |
| 3,872,280 | 3/1975 | Jun Van Dalen | 219/274 |
| 4,037,353 | 7/1977 | Hennart et al. | 219/274 |
| 4,191,743 | 3/1980 | Klemm et al. | 424/28 |
| 4,214,146 | 7/1980 | Schimanski | 219/274 |

FOREIGN PATENT DOCUMENTS

| | | | |
|---|---|---|---|
| 2516021 | 2/1976 | Fed. Rep. of Germany | 36/43 |
| 2295710 | 7/1976 | France | 36/43 |
| 533637 | 2/1941 | United Kingdom | 219/274 |

*Primary Examiner*—James C. Cannon
*Attorney, Agent, or Firm*—Wenderoth, Lind & Ponack

[57] ABSTRACT

A molded body for generating an aerosol for treating athlete's foot comprised of a vegetable oil composition which is solid at room temperature. The composition may additionally contain a metal catalyst for accelerating the oxidation of the vegetable oil or an organic catalyst for retarding the progress of the oxidation of the vegetable oil. The molded body becomes molten on being heated and then generates an aerosol which treats athlete's foot. Being solid at ordinary temperatures, this aerosol generating body is easy to handle and safe for use in an athlete's foot treating apparatus.

10 Claims, 1 Drawing Figure

4,340,053

MOLDED BODY COMPRISING VEGETABLE OIL FOR GENERATING AEROSOL FOR TREATING ATHLETE'S FOOT

BACKGROUND OF THE INVENTION

Athlete's foot is a skin disease generally known as pompholyx ringworm, and appears on soles, palms and/or interdigital surfaces of the hands and feet. It is caused by a certain thread fungus or Trichophyton. Favus, which causes white and round desquamating macula, and ringworm as well, are all similarly classified. They are also known as dartre or Herpes.

In Japan, for example, athlete's foot readily spreads during the rainy season and summer. Various medicines have been proposed for treating athlete's foot. In many cases, however, this disease subsides during the winter but regains its strength around April or May of the next year. The same phenomenon is seen all over the world.

It is thus an object of the present invention to provide an effective treatment for athlete's foot and it is a further object of this invention to provide an aerosol generating molded body for the treatment of athlete's foot which can be used easily and safely.

SUMMARY OF THE INVENTION

This invention relates a molded body for generating an aerosol for treating athlete's foot. The aerosol is generated by heating a vegetable oil composition which is solid at room temperature, with or without a catalyst which accelerates or restrains the oxidation of the vegetable oil. The generated aerosol is brought into contact with a part of the body which is afflicted by athlete's foot at between 40° C. and 80° C. Alternatively, the aerosol is brought into contact with the afflicted part of the body under after it has been condensed and activated by means of supersonic waves.

DETAILED DESCRIPTION OF THE INVENTION

Figure 1:
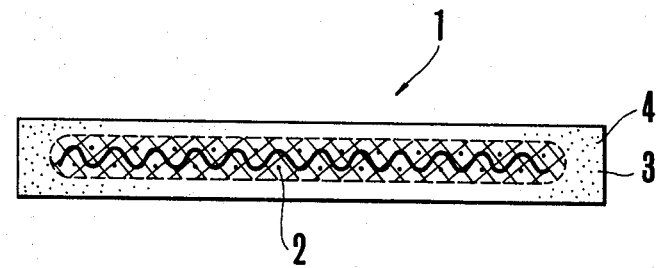

The molded body for generating an aerosol for treating athlete's foot according to this invention consists of a formed vegetable oil composition which is solid at room temperature and which upon heating generates an aerosol or vapor, including said vegetable oil and oxidation products thereof. The vegetable oil composition can comprise one or more of vegetable oils, vegetable fats, hardened vegetable oils and hardened vegetable fats. Where liquid fats or oils are used, they can be thickened to be rendered solid at room temperature.

Additionally, the vegetable oil composition can comprise a metal catalyst for accelerating the oxidation of the vegetable oils or an organic catalyst for retarding the oxidation of the vegetable oils, vegetable fats, hardened vegetable oils and hardened vegetable fats etc. This aerosol generating molded body is easy to use and safe. By heating this molded body in a vessel placed in an enclosure, an aerosol is generated to form an atmosphere thereof within the enclosure. Then, a part of the body affected by athlete's foot is exposed to the atmosphere at between 40° C. and 80° C.

The FIGURE depicts a molded body of this invention.

Next, an embodiment of this invention will be described in detail by reference to the accompanying drawing. The FIGURE is a cross-sectional view of a molded body for generating an aerosol for treating athlete's foot according to this invention. In this FIGURE, reference numeral 1 designates the molded body, 2 a wire net coated with asbestos, 3 a mixture of vegetable oils and 4 a catalyst.

For ease of understanding, discussion here will be confined to the treatment of athlete's foot.

As mentioned before, this aerosol generating molded body assumes a solid form at ordinary temperatures. Therefore, the molten body in the vessel becomes solid again as it cools after generating the aerosol. Unlike liquid oils, the solidified oil does not leave the vessel even when the treating apparatus is moved, eliminating the risk that the spilled oil ignites on being heated.

When the vegetable oil, vegetable fat, hardened vegetable oil or hardened vegetable fat is brought into contact with oxygen or air, the oxygen absorption is not quite noticed at first, but after certain time the absorption takes place.

The electronic structural formula of oxygen molecule is as follows:

$$:\ddot{O}:\ddot{O}:$$

As $O_2$ is considered to be the combination of two free radicals, it is difficult to dissociate oxygen molecule into two oxygen atoms. The oxidation of the vegetable oil is generally considered to be caused by molecular oxygen {oxygen molecule (gaseous $O_2$), absorbed molecule ($O_2$, $O^{-2}$), excited oxygen ($O_2$ in singlet state)}, atomic oxygen lattice oxygen ($O^{2-}$, superoxide ion), {adsorbed oxygen ($O^-$, $O^{2-}$), oxygen atom (O)} peroxy compound {peracid (RCOOH), hydroperoxide (ROOH), peroxyradical (ROO)}, and anions ($OH^-$).

In order to accelerate the oxidation of vegetable oil, vegetable fat, hardened oil, or hardened fat, the main component of which comprises glyderides of linoleic acid, oleic acid, palmitic acid, stearic acid, arachidic acid and the like, the existence of such forms of oxygen or compounds thereof, as described above, is required. In the present invention, a catalyst can also be added to the vegetable oil, vegetable fat, hardened oil or hardened fat. The catalyst is used to accelerate or control the oxidation of the vegetable oil, vegetable fat, hardened oil or hardened fat. The catalyst comprises a metal catalyst and/or an organic catalyst.

Thus the oxidation of the vegetable oil, vegetable fat, hardened oil and hardened fat is accelerated and controlled respectively, to generate a proper quantity of oxidation product vapor in the form of an aerosol. The oxidation product vapor consists mainly of hydroperoxides, alcohols, aldehydes, ketones, various decomposed substances, acids and the like.

The saturated fatty acid contained in large quantity in the vegetable oil, vegetable fat, hardened oil and hardened fat has properties of both the alkyl radical (R) and carboxyl radical (—COOH). The unsaturated fatty acid is identical with the saturated fatty acid in forming salts, esters, acid anhydrides and acid amides, but the salt of the unsaturated fatty acid is generally more soluble in a solvent than that of the saturated fatty acid which the same carbon number.

The purpose of the oxidation of the vegetable oil, vegetable fat, hardened oil and hardened fat is in order to generate the alkyl radical, that is, free radical of the fatty acid by making the fatty acid glyceride of the vegetable oil react with an oxygen molecule or its compound. It is sufficient for the present purpose when this reaction proceeds only slightly.

$$RH + O_2 \rightarrow R^0 + HO_2 \quad (1)$$

When a small quantity of $R^0$ is generated, the reaction proceeds smoothly afterwards.

$$R^0 + O_2 \rightarrow R-OO^0 \quad (2)$$

Namely, the $R^0$ generated in the formula (1) acts as a nucleus and repeats the reaction of the formula (2) to change RH to the so-called hydroperoxide via a chain reaction. In short, the first stage of the oxidation of the vegetable oil, vegetable fat, hardened oil and hardened fat is the generation of hydroperoxide.

When this hydroperoxide is brought in contact with the afflicted part, the athlete's foot germs existing therein are destroyed. Within three minutes, pain and itching disappear.

In the first stage of the oxidation reaction, hydroperoxide is generated by the free radical reaction, and the reaction is activated by heat, catalysts, ultrasonic waves and by various kinds of molecules which decompose to generate free radicals under that condition, but the mechanism is complex.

$$RH \text{ activation} \rightarrow R^0 - (H) \quad (3)$$

$$RH + O_2 \rightarrow R^0 + HO_2 \quad (1)$$

As shown in the formula (3), the reaction begins when sufficient energy to activate a part of the fatty acid glyceride is imparted by heat and the like. The formula (3) may be estimated to be the same as the formula (1). The largest part of the oxygen which is adsorbed at the early stage of the reaction is thought to generate hydroperoxide and during the induction period of the reaction, hydroperoxide is considered to be gradually accumulated. Generally, in the auto-oxidation reaction of the fatty acid glyceride which contains no catalyst i.e. is composed of impurities, the induction period precedes. Sometimes the reaction is accelerated or controlled by the existence of a very small quantity of catalyst, including impurities.

The $R^0$, which is generated from the fatty acid glyceride (RH) of the vegetable oil, acts as a nucleus to generate R—OOH according to the formula (2), but this hydroperoxide is stable only at a low temperature. When the temperature is raised, it decomposes as follows, and it sometimes occurs that two or more $R^0$ are regenerated from one $R^0$, $$R-OOH \rightarrow R^0 + O^0H$$

It is accepted generally that in the range 140°–180° C. the adsorbed amount of oxygen is doubled with every 10° C. increment.

The weakest bond in the thus generated hydroperoxide is the C—C bond, and accordingly, the hydroperoxide undergoes cleavage to generate alcohols, aldehydes, ketones, various kinds of acid.

Summarizing the above-mentioned oxidation mechanisms, the generation of hydroperoxide is activated by heat, catalyst and ultrasonic waves.

| Beginning of chain reaction | $RH \rightarrow R^0 + (H^0)$ |
| Transmission of chain reaction | $R^0 + O_2 \rightarrow RO_2^0$ |
| | $RO_2 + RH \rightarrow RO_2^0H + R^0$ |
| Termination of chain reaction | $R^0 + R^0 \rightarrow RH + R(-H)$ |
| | $RO_2 . OH \rightarrow ROH + O_2$ |
| | $R^0 + R^0 \rightarrow R - R$ |
| Decomposition of hydroperoxide | |
| Thermal cracking | $ROOH \rightarrow R + O^0H$ |
| Cracking by acid catalyst | $ROOH \rightarrow RO^\oplus + OH^\ominus$ |
| Cracking by base catalyst | $ROOH \rightarrow ROO^\ominus + H^\oplus$ |
| Cracking by metal catalyst | $ROOH \rightarrow RO^\ominus + O^0H + (M^{2\oplus})$ |
| Cracking by organic catalyst | $ROOH \rightarrow RO^0 + O^0H$ |

As shown in the formulae as described above, hydroperoxide decomposes in a complicated way according to the conditions for generating various kinds of vapor. In this specification, these vapors are called "oxidation product vapors in the form of aerosol" generically. In the thus generated oxidation product vapor in the form of an aerosol, aldehydes, ketones, lactone oxide, glycol acid, valeric acid and acetic acid are the main components, and also various decomposed substances are contained.

When the oxidation product vapor in the form of aerosol including hydroperoxide is brought in contact with the part of hands or feet afflicted by athlete's foot, the oxidation product vapor reacts with the athlete's foot germs and, consequently within three minutes, although it differs according to the property of the germs, the afflicted area assumes a moist powdery appearance or a white desquamation of 3–8 mm which looks like spider's thread when the oxidation product vapor reaches the depth of the afflicted part. When the treatment is repeated until the afflicted part attains the above-mentioned state, athlete's foot is dramatically cured.

In the present invention, there may be used any vegetable oil, vegetable fat, hardened oil or hardened fat which contains a glyceride of linoleic acid, oleic acid, palmitic acid, stearic acid or arachidic acid as the main component. Therefore, any of fats, hardened oils, drying oils, semi-drying oils and non-drying oils may be used separately or in a mixed state. However, the vegetable oil, vegetable fat, hardened oil or hardened fat used in the present invention preferably has the chemical composition and properties as shown below:

| Specific gravity 15°/15° | 0.911–0.943 |
| Refractive index | 1.468/15°–1.478/15° |
| Saponification value | 186–215 |
| Iodine value | 83–180 |
| Acid value | 1–20 |
| Unsaponifiable matter | 0.2–3% |
| Melting point (mixed fatty acids) | 13–70° C. |

As the vegetable oil, drying oils such as linseed oil, soybean oil, tung oil, hemp-oil, etc., semi-drying oils such as cotton seed oil, benne oil, rape seed oil, rice-bran oil, etc. and non-drying oil such as camellia oil, arachis oil, olive oil, castor oil, etc. may be used. As the vegetable fat, Japan wax, coconut oil, palm oil or the like may be used. And the hardened oil which as used herein is the hydrogeneration product of any of the oils or fats which were exemplified above.

These vegetable oils, vegetable fats, hardened oils and hardened fats usually oxidize with an increase in temperature. They also readily oxidize upon exposure to light and catalyst.

According to this invention, catalyst may be added to the vegetable oil, vegetable fat, hardened oil and hardened fat to accelerate or control the oxidation thereof. There are two types of catalysts; one is a metal catalyst which accelerates the oxidation of the vegetable oil, vegetable fat, hardened oil and hardened fat and the other is an organic catalyst which controls the oxidation of the vegetable oil, vegetable fat, hardened oil and hardened fat. The metal catalyst includes Fe, Mn, Al, Zn, Ni, Co, Ca, V, Pt, Pd, Au and their oxides. The organic catalyst includes seeds, or powder thereof, of leguminous, sesame, liliaceous, cruciferous and other plants.

Addition of such catalyst not only accelerates and controls the oxidation of the vegetable oil, vegetable fat, hardened oil or hardened fat, but also lowers the oxidation temperatures thereof as shown in the Examples which follow. The lowered oxidation temperature, in turn, facilitates the control of aerosol temperature. The acceleration and control of vegetable oil oxidation, attained by the addition of the catalyst, prevents the decomposition of hydroperoxide resulting from the oxidation and, thereby, facilitates obtention of the necessary concentration of hydroperoxide in the aerosol.

The present invention will be understood more readily by reference to the following examples. The examples, however, are intended to illustrate the invention and are not to be construed as limiting the scope of the invention.

EXAMPLE 1

2 g of cotton-like asbestos, previously dispersed in water, is applied to both sides of a 10 cm² wire net (wire diameter 0.25 mm and mesh size 1.5 mm²) and dried. 30 g of hardened coconut oil, having a melting point of 50° C., 5 g of olive oil, 10 g of sesame oil, 5 g of soybean oil, 10 g of linseed oil, 0.3 g of palladium black and 2 g of spring onion seed were mixed and melted on a hot bath at 70° C. Meanwhile, the asbestos-coated wire net was placed in a mold which is larger than the net. The obtained hot liquid was poured, and allowed to cool, in the mold, whereby a solid body which readily generates the desired curing aerosol and is easy and safe to handle was obtained.

EXAMPLE 2

A wire net prepared in the same manner as in Example 1 was placed in a mold. 30 g of hardened coconut oil, having a melting point of 60° C., 10 g of peanut oil, 10 g of sesame oil, 10 g of soybean oil, 10 g of rape oil, 10 g of castor oil, 0.1 g of platinum black, 0.2 g of metallic aluminum, 0.2 g of zinc oxide, and 8 g of crushed rapeseed were mixed and melted on a hot bath at 80° C. The obtained hot liquid was poured, and allowed to cool in the mold, to produce an aerosol generating body similar to the one in Example 1.

EXAMPLE 3

A wire net prepared in the same manner as in Example 1 was placed in a mold. 30 g of hardened coconut oil, having a melting point of 70° C., 10 g of sesame oil, 10 g of corn oil, 10 g of rice-bran oil, 10 g of olive oil, 0.2 g of palladium black, 0.1 g of vanadium oxide, 0.1 g of manganese oxide, 10 g of crushed leekseed, and 0.05 g of gold leaf were mixed and melted on a hot bath at 80° C. The obtained hot liquid was poured, and allowed to cool, in the mold, to produce an aerosol generating body similar to the one in Example 1.

The aerosol generating molded body thus obtained is put in a plate, in which it is melted under heat to generate an aerosol. This aerosol generating body is easy and safe to handle, and can be used with apparatus for treating not only athlete's foot but also hemorrhoids and neuralgia. Further, the aerosol generating body of this invention can be obtained in any size according to the size of the treating apparatus with which the body is used.

The above description concerns the aerosol generating body having a core of asbestos-coated wire net, but a molded body without such core can be manufactured and used, as well.

What is claimed is:

1. A method for treating athlete's foot fungal infection which comprises contacting a portion of the skin afflicted with such fungus with an aerosol produced by heating a molded body comprising a vegetable oil containing composition which is solid at room temperature and which melts upon heating to generate said aerosol, said aerosol comprising an effective amount of oxidation products of such vegetable oil to destroy said fungus.

2. The method according to claim 1 wherein said fungus is of the genus Trichophyton.

3. The method according to claim 1 wherein said molded body comprises said vegetable oil composition deposited on a wire mesh substrate.

4. The method according to claim 1 wherein said oxidation products comprise hydroperoxides.

5. The method according to claim 4 wherein said composition is heated to 40° C. to 80° C.

6. The method according to claim 5 wherein said composition contains a metal oxidation catalyst and organic oxidation inhibitor or both.

7. A molded body for treating athlete's foot comprising a vegetable oil containing composition which is solid at room temperature and which melts upon heating to form an aerosol containing an effective amount of oxidized products of said vegetable oil to treat athlete's foot.

8. The molded body according to claim 7 wherein said vegetable oil has the following physical properties:

| | |
|---|---|
| Specific gravity 15°/15° | 0.911–0.943 |
| Refractive index | 1.468/15°–1.478/15° |
| Saponification value | 186–215 |
| Iodine value | 83–180 |
| Acid value | 1–20 |
| Unsaponifiable matter | 0.2–3% |
| Melting point (mixed fatty acids) | 13–70° C. |

9. The molded body according to claim 7 wherein said composition further contains a metal oxidation catalyst and organic oxidation inhibitor or both.

10. The molded body according to claim 7 wherein said vegetable oil is deposited on a wire mesh substrate.

* * * * *